(12) United States Patent
Cadwalader et al.

(10) Patent No.: US 8,487,287 B2
(45) Date of Patent: Jul. 16, 2013

(54) WRAPAROUND STANDOFF RADIATION ATTENUATION SHIELD

(75) Inventors: John A. Cadwalader, Overland Park, KS (US); William W. Orrison, Las Vegas, NV (US)

(73) Assignee: Worldwide Innovations & Technologies, Inc., Kansas City, KS (US)

( * ) Notice: Subject to any disclaimer, the term of this patent is extended or adjusted under 35 U.S.C. 154(b) by 80 days.

(21) Appl. No.: 12/852,287

(22) Filed: Aug. 6, 2010

(65) Prior Publication Data

US 2011/0095209 A1 Apr. 28, 2011

Related U.S. Application Data (60) Continuation-in-part of application No. 12/348,785, filed on Jan. 5, 2009, now Pat. No. 8,022,378, which is a continuation of application No. 11/796,764, filed on Apr. 30, 2007, now Pat. No. 7,473,919, which is a division of application No. 10/997,777, filed on Nov. 24, 2004, now Pat. No. 7,211,814.

(51) Int. Cl.
*G21F 3/00* (2006.01)

(52) U.S. Cl.
USPC ............... 250/515.1; 250/505.1; 250/519.1; 378/193; 378/203; 600/1

(58) Field of Classification Search
USPC .......... 250/505.1, 506.1, 507.1, 515.1, 516.1, 250/517.1, 519.1; 378/193, 203; 600/1, 2, 600/3
See application file for complete search history.

(56) References Cited

U.S. PATENT DOCUMENTS

| | | | |
|---|---|---|---|
| 3,419,006 | A | 12/1968 | King |
| 3,514,607 | A | 5/1970 | Webster |
| 3,935,099 | A | 1/1976 | Weaver et al. |
| 4,286,170 | A | 8/1981 | Moti |
| 4,558,093 | A | 12/1985 | Hatzenbuhler et al. |
| 4,621,808 | A | 11/1986 | Orchard et al. |
| 4,670,658 | A | 6/1987 | Meyers |
| 4,938,233 | A | 7/1990 | Orrison, Jr. |
| 5,247,182 | A | 9/1993 | Servant et al. |

(Continued)

FOREIGN PATENT DOCUMENTS

| | | |
|---|---|---|
| DE | 30 17 640 | 11/1981 |
| DE | 30 17 640 A1 | 11/1981 |

(Continued)

OTHER PUBLICATIONS

Fricke et al., "In-Plane Bismuth Breast Shields for Pediatric CT: Effects on Radiation Dose and Image Quality Using Experimental and Clinical Data", American Journal of Roentgenology, vol. 180, Feb. 2003, pp. 407-411 (5 pages).

(Continued)

*Primary Examiner* — Nicole Ippolito
(74) *Attorney, Agent, or Firm* — Foley & Lardner LLP (57) ABSTRACT

A system for attenuating a primary radiation beam applied to a target area on a patient for generating an image of the target area during radiological examination includes a barrier formed of a radiation attenuation material and positionable over the target area to partially attenuate the primary radiation beam before the primary radiation beam reaches the target area. The barrier is configured to substantially extend around an entire periphery of the patient. The system also includes a buffer positionable between the barrier and the patient for offsetting the barrier from the patient. The buffer includes at least one flexible bag configured to retain a fluid. The at least one flexible bag is configured to improve the clarity of the image generated during the radiological examination.

21 Claims, 7 Drawing Sheets

U.S. PATENT DOCUMENTS

| | | | |
|---|---|---|---|
| 5,278,219 A | 1/1994 | Lilley et al. | |
| 5,417,225 A | 5/1995 | Rubenstein et al. | |
| 5,523,581 A | 6/1996 | Cadwalader | |
| 5,525,408 A | 6/1996 | Weir et al. | |
| 5,548,125 A | 8/1996 | Sandbank | |
| 6,048,379 A | 4/2000 | Bray et al. | |
| 6,153,666 A | 11/2000 | Lagace | |
| 6,320,938 B1 | 11/2001 | Hopper | |
| 6,429,432 B1 | 8/2002 | McNaught et al. | |
| 6,481,888 B1 | 11/2002 | Morgan | |
| 6,674,087 B2 | 1/2004 | Cadwalader et al. | |
| 7,099,427 B2 | 8/2006 | Cadwalader et al. | |
| 7,211,814 B2 | 5/2007 | Cadwalader et al. | |
| 7,473,919 B2 | 1/2009 | Cadwalader et al. | |
| 7,767,990 B2 | 8/2010 | Cadwalader et al. | |
| 2002/0109107 A1* | 8/2002 | Goldstein | 250/505.1 |
| 2002/0148980 A1 | 10/2002 | Cadwalader et al. | |
| 2003/0209672 A1* | 11/2003 | Nelson et al. | 250/394 |
| 2004/0105525 A1* | 6/2004 | Short et al. | 378/98.8 |
| 2008/0149864 A1* | 6/2008 | Hargrove | 250/515.1 |

FOREIGN PATENT DOCUMENTS

| | | |
|---|---|---|
| DE | 91 03 451 U1 | 9/1991 |
| FR | 2 439 460 | 10/1978 |
| FR | 2439460 | 10/1978 |

OTHER PUBLICATIONS

International Search Report and Written Opinion for Application No. PCT/US2005/042685, mailing date Apr. 10, 2006, date received Apr. 13, 2006. 14 pages.

Notice of Allowance for U.S. Appl. No. 10/997,777, mail date Jan. 10, 2007, 4 pages.

Notice of Allowance for U.S. Appl. No. 11/796,764, mail date Sep. 8, 2008, 4 pages.

Office Action for U.S. Appl. No. 10/997,777, mail date Sep. 22, 2006, 6 pages.

Office Action for U.S. Appl. No. 11/796,764, mail date Mar. 27, 2008, 7 pages.

Office Action for U.S. Appl. No. 12/348,785, mail date Nov. 22, 2010, 6 pages.

Office Action for U.S. Appl. No. 90/010,808, mail date Jul. 7, 2010, 8 pages.

Office Action for U.S. Appl. No. 90/010,808, mail date Oct. 27, 2010, 6 pages.

Office Action for U.S. Appl. No. 90/010,809, mail date Jul. 7, 2010, 7 pages.

Printout of copyright registration data for the Feb. 2003 issue of the American Journal of Roentgenology obtained from the U.S. Copyright Office searchable copyright registrations database indicating publication data of Jan. 22, 2003, 2 pages.

Promotional material titled Xenolite Radiation Protection Garments by DuPont Technology "Less Weight . . . Full Protection," Manufactured by Lite Tech, Inc., 18 Depot Street Bridgeport, PA 19405, undated (6 sheets), 2010.

Request for Ex Parte Reexamination of U.S. Patent No. 7,473,919 including exhibits, filed Jan. 5, 2010, 77 pages.

Request for Ex Parte Reexamination of U.S. Patent No. 7,211,814 including exhibits, filed Jan. 5, 2010, 123 pages.

\* cited by examiner

WRAPAROUND STANDOFF RADIATION ATTENUATION SHIELD

CROSS REFERENCE TO RELATED PATENT APPLICATIONS

The present application is a continuation-in-part of U.S. application Ser. No. 12/348,785, filed Jan. 5, 2009, which is a continuation application of U.S. application Ser. No. 11/796,764, filed Apr. 30, 2007, now U.S. Pat. No. 7,473,919 (issued Jan. 6, 2009), which is a divisional application of U.S. application Ser. No. 10/997,777, filed Nov. 24, 2004, now U.S. Pat. No. 7,211,814 (issued May 1, 2007), the entire disclosures of which are hereby incorporated by reference.

BACKGROUND

The present disclosure relates generally to systems for and methods of attenuating radiation. More particularly, the present disclosure relates to systems for and methods of attenuating radiation during a radiological examination of a patient.

Radiation barriers or shields are used to attenuate (e.g., deflect, absorb, etc.) the flux of electromagnetic radiation originating from a radiation source and directed towards a patient. Radiation can have beneficial and/or negative effects. One beneficial effect of radiation relates to radiological examinations. For purposes of this disclosure, the phrase radiological examination refers generally to any procedure wherein radiation is applied to a patient for the purpose of producing an image or representation of the article. Radiological examinations may provide a non-invasive means capable of obtaining an image of the internal composition of the patient. Radiological examinations may be employed in a variety of applications including, but not limited to, medical procedures.

A wide array of medical procedures exist where radiological examinations are employed to obtain an image of the anatomy of a patient or portions thereof. For example, portions of a patient's anatomy may be irradiated during: (i) diagnostic procedures (e.g., Computed Tomography (CT) scanning, x-ray photography, or any other imaging procedure) allowing non-invasive investigation of anatomical regions of a patient (e.g., internal tissue, organs, etc.); or (ii) various invasive procedures, such as the fluoroscopic guidance and/or manipulation of instruments during surgical procedures (e.g., CT fluoroscopy, etc.).

To obtain an image through a radiological examination, a primary radiation beam (i.e., entrance radiation) is applied to the patient. Preferably, radiation is selectively focused on to those areas to be examined (i.e., target areas) to minimize the patient's overall radiation exposure. Typically, the target areas are irradiated directly without any obstruction or impairment provided between the primary radiation beam and the patient. It is generally known to cover those areas above and/or below the target area that are not being examined (i.e., secondary areas) with a radiation barrier or shield to prevent and/or reduce radiation exposure for those areas. Such shields are formed of a radiation attenuating material and are often placed directly upon the patient.

It has been discovered that in certain procedures limited imaging of the patient can still be generated when a barrier or shield (made of a radiation attenuating material) is placed over the target area (i.e., coincident with the primary radiation beam). The radiation attenuation material absorbs much of the primary radiation beam, but allows an amount (sufficient to generate an image of the patient) to penetrate through and subsequently penetrate the patient. Placing the shield over the target area reduces the amount of radiation exposure realized by the patient. This method of reducing radiation exposure may be particularly beneficial during fluoroscopy procedures during which particularly sensitive areas (e.g., male or female reproductive regions, female breast tissue, etc.) of a patient are exposed to a primary radiation beam.

However, it has further been discovered that it is often difficult (if not impossible) to sufficiently examine certain regions of the article when a radiation attenuation material is positioned coincident with the primary radiation beam and over the target area. For example, placing a radiation attenuation material on the surface of the patient prevents a clear and/or accurate image of the surface (or regions slightly below the surface) from being obtained. Such examination limitations are due to x-ray glare (e.g., noise, scatter, artifact, etc.), referred to in this disclosure generally as interference, generated when radiation encounters the radiation attenuation material. This interference hinders a user's ability to obtain a clear image of the patient and therefore cannot be used during the radiological examination.

Thus, there is a need for a radiation attenuation system that may be used during a radiological examination to reduce the amount of radiation exposure realized by a patient undergoing the examination. Also, there is a need for a radiation attenuation system that may be positioned coincident to the primary radiation beam to protect the target area (i.e., the area of examination) from increased radiation exposure. Further, there is a need for a radiation attenuation system that may be used during a radiological examination without allowing the interference (caused when radiation encounters a radiation attenuation material) from interfering with the clarity and/or accuracy of the generated image of a patient. Further yet, there is a need for a radiation attenuation system that reduces the amount of radiation exposure for personnel present during a radiological examination. Further still, there is a need for a radiation attenuation system that is relatively adaptable for use with a variety of radiological examinations. It would be desirable to provide for a radiation attenuation system capable of satisfying one or more of these or other needs.

SUMMARY

According to an exemplary embodiment, a system for attenuating a primary radiation beam applied to a target area on a patient for generating an image of the target area during radiological examination includes a barrier formed of a radiation attenuation material and positionable over the target area to partially attenuate the primary radiation beam before the primary radiation beam reaches the target area. The barrier is configured to substantially extend around an entire periphery of the patient. The system also includes a buffer positionable between the barrier and the patient for offsetting the barrier from the patient. The buffer includes at least one flexible bag configured to retain a fluid. The at least one flexible bag is configured to improve the clarity of the image generated during the radiological examination.

According to another exemplary embodiment, a system for attenuating a primary radiation beam applied to a target area on a patient for generating an image of the target area during radiological examination includes a barrier formed of a radiation attenuation material and positionable over the target area to partially attenuate the primary radiation beam before the primary radiation beam reaches the target area. The system also includes a buffer positionable between the barrier and the patient for offsetting the barrier from the patient. The buffer includes at least one flexible bag configured to retain a fluid.

The system further includes a valve coupled to at least one flexible bag to allow a user to selectively inflate and deflate the at least one flexible bag for adjusting a distance between the barrier and the target area. The at least one flexible bag is configured to improve the clarity of the image generated during the radiological examination According to another exemplary embodiment, a method of performing a radiological examination of a target area on a patient with a primary radiation beam to generate an image of the target area includes placing a radiation attenuation system on the patient. The radiation attenuation system includes a barrier formed of a radiation attenuation material and a buffer formed of at least one flexible bag configured to retain a fluid. The method also includes aligning the barrier to be in-line with the primary radiation beam so that the primary radiation beam passes through the barrier before reaching the target area. The method further includes positioning the at least one flexible bag between the barrier and the target area.

DETAILED DESCRIPTION

Referring generally to the FIGURES, a radiation attenuation system for use during radiological examinations is disclosed according to an exemplary embodiment. The radiation attenuation system is configured to attenuate radiation that would otherwise be received by a patient and allow for a radiological examination in a number of applications, environments, and configurations. Generally the system includes a first portion or layer for attenuating radiation before reaching a patient and a second portion or layer for buffering (e.g., displacing, offsetting, elevating, spacing apart, etc.) the first portion from the patient undergoing the radiological examination. According to an exemplary embodiment, at least the first portion (i.e., the radiation attenuating portion) is configured to extend laterally around the entire periphery of the patient so that the radiation attenuation system can provide at least some level of protection for the patient throughout an entire radiological examination (e.g., throughout a complete revolution of a CT scanner, etc.). As detailed below, the configuration of the first portion (e.g., the shape, the radiation attenuation effectiveness, the thickness, the continuity, etc.) may vary as the first portion extends around the patient.

The radiation attenuation system disclosed herein is configured for in-plane shielding wherein a primary radiation beam is partially blocked by the radiation attenuation system before reaching a target area on the patient (i.e., the area on the patient for which an image is to be obtained). The radiation attenuation system reduces the radiation dose realized by the tissue at the target area while allowing enough radiation to pass to be able to generate an image. By providing a buffer region (i.e., the second portion) between the first portion and the patient, improved imaging (e.g., visualization, examination, image capturing, image displaying, etc.) of the target area of the patient can be achieved. For example, providing a buffer region between the radiation attenuating portion and the patient may allow for imaging of internal regions of the patient as well as other regions of the patient (e.g., surface regions, regions slightly below the surface of the article, etc.) that may otherwise be difficult to examine due to glare (e.g., noise, scatter, artifact, etc.), referred to in this disclosure generally as interference, generated when radiation encounters the first portion.

The radiation attenuation system may be used with any medical procedure (e.g., fluoroscopy procedures, Computed Tomography (CT) procedures (e.g., invasive (fluoroscopy) and/or noninvasive (scanning)), x-ray photography procedures, and/or any other image producing medical procedure using radiation, etc.) involving a radiological examination wherein radiation is applied to the anatomy of a patient (or portions thereof) to generate an image on an appropriate display (e.g., monitor, screen, x-ray film, etc.). The radiation attenuation system can be placed upon, near, under, or otherwise about the patient undergoing the radiological examination. The radiation attenuation system lessens or otherwise reduces the amount of radiation (e.g., primary radiation beam, incidental scatter radiation, etc.) realized by a patient and/or personnel (e.g., physicians, surgeons, technicians, etc.) present during the procedures.

Figure 1:
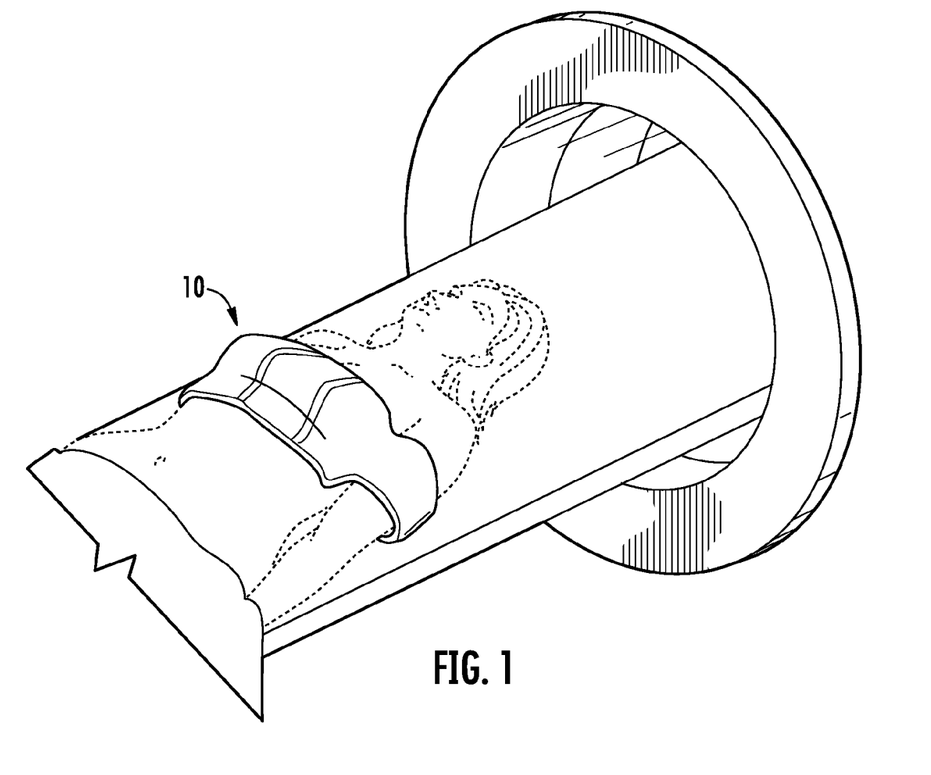
FIG. 1 is a perspective view of a radiation attenuation shield according to an exemplary embodiment shown on a patient.
Figure 2:
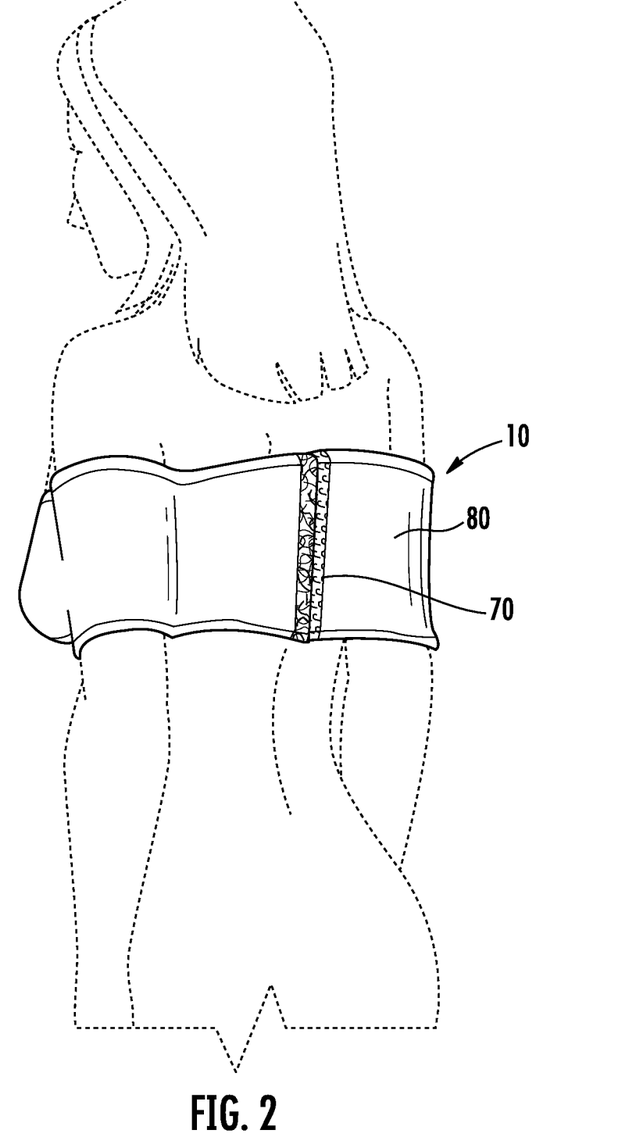
FIG. 2 is a rear view of the radiation attenuation shield illustrated in FIG. 1 shown on a patient.
Figure 3:
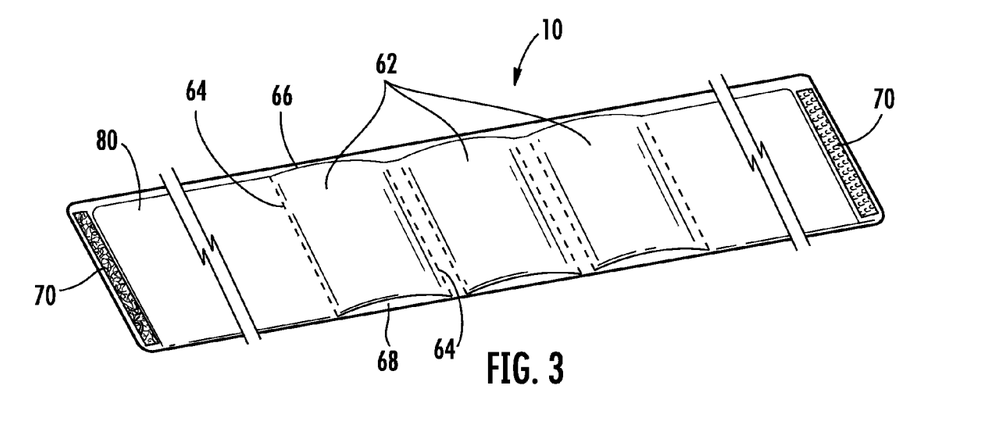
FIG. 3 is a perspective view of the radiation attenuation shield illustrated in FIG. 1

Referring to FIGS. 1 through 3, the radiation attenuation system is shown according to an exemplary embodiment as a shield 10 configured to protect the breast area of a female patient undergoing a CT procedure from undue radiation exposure. Shield 10 provides a relatively convenient and functionally integrated means of attenuating radiation while allowing for a thorough examination of multiple regions of the article. While shield 10 is illustrated as being used as a shield configured to cover the chest and/or abdomen area of a female patient, shield 10 is equally applicable for use with male patients. Further, shield 10 is applicable for use with any radiological examination procedure wherein radiation is applied to a patient for the purposes of producing an image of the patient (e.g., to shield a gonadal region, thyroid region, etc.). Further still, while shield 10 will be described as protecting a patient during a medical procedure, the scope of the appended claims is intended to encompass shields employed in any application (not limited to medical applications) that uses radiation to generate an image of an article.

Figure 4:
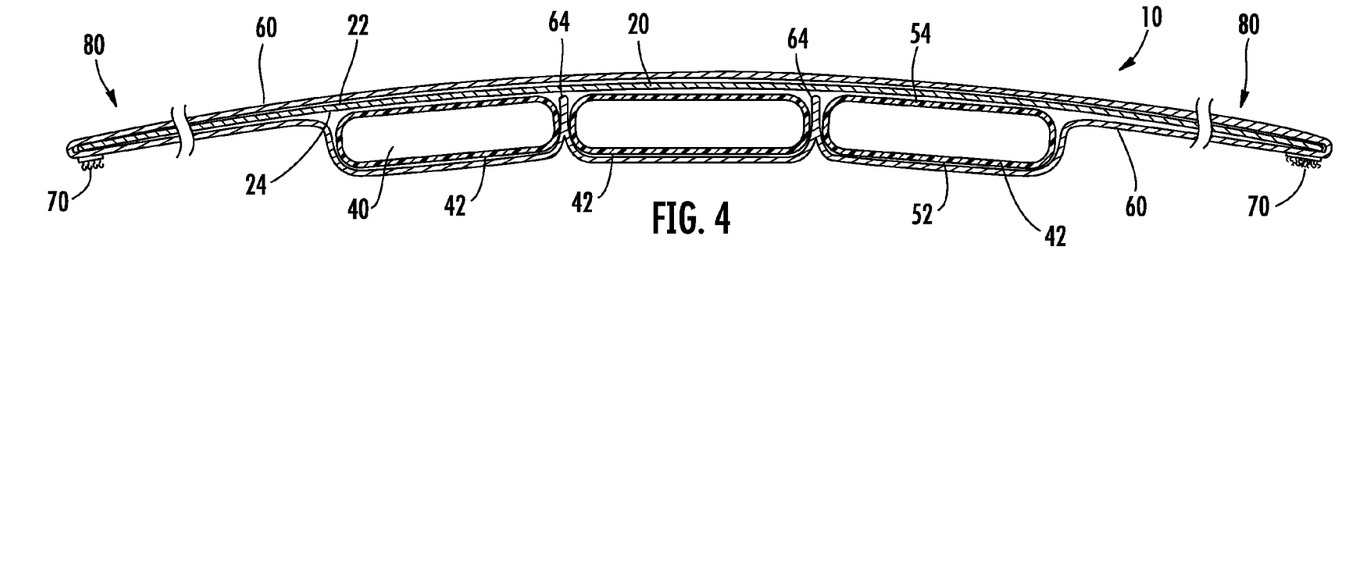
FIG. 4 is a cross sectional view of the radiation attenuation shield illustrated in FIG. 3 showing a buffer layer as a plurality of fluid-filled bags inflated to a first position.

FIG. 4 shows a cross sectional view of shield 10 according to an exemplary embodiment. Shield 10 includes a first portion or layer (e.g., platform, web, matrix, film, pad, radiation attenuating material, etc.), shown as a barrier 20, a second portion or layer (e.g., filler, spacer, lifter, relatively non-radiation attenuating material, etc.), shown as a buffer 40, and a third portion or layer (e.g., housing, casing, coating, skin, outer material, membrane, etc.), shown as a cover 60. The attenuation of radiation is provided by barrier 20, while buffer 40 provides a substantially non-radiation attenuating boundary or zone between barrier 20 and the surface of the patient. Cover 60 forms the exterior portion or surface (e.g., exposed surface, etc.) of shield 10 and may be useful in retaining and/or supporting buffer 40 relative to barrier 20, protecting barrier 20 and/or buffer 40 from contaminants (e.g., fluids, particles, etc.), providing enhanced comfort for a patient, and/or, improving the overall durability of shield 10.

Referring back to FIGS. 1 and 2, shield 10 is positioned on the patient so that barrier 20 can extend laterally around the entire periphery of the patient to provide at least some level of protection for the patient throughout a complete revolution of a CT scanner. As such, in addition to being disposed along the chest area of the patient, barrier 20 is also disposed along the sides and back of the patient to further protect the patient from undue radiation exposure. In an application where the patient is lying on a table, such as in FIG. 1, barrier 20 is intended to be positioned between the patient and the table. Shield 10 may be configured to loosely drape around the patient, or alternatively, may be configured to be worn by a patient as shown in FIG. 2 (e.g., by being sized to fit the patient and/or by being adjustable, etc.).

Figure 5:
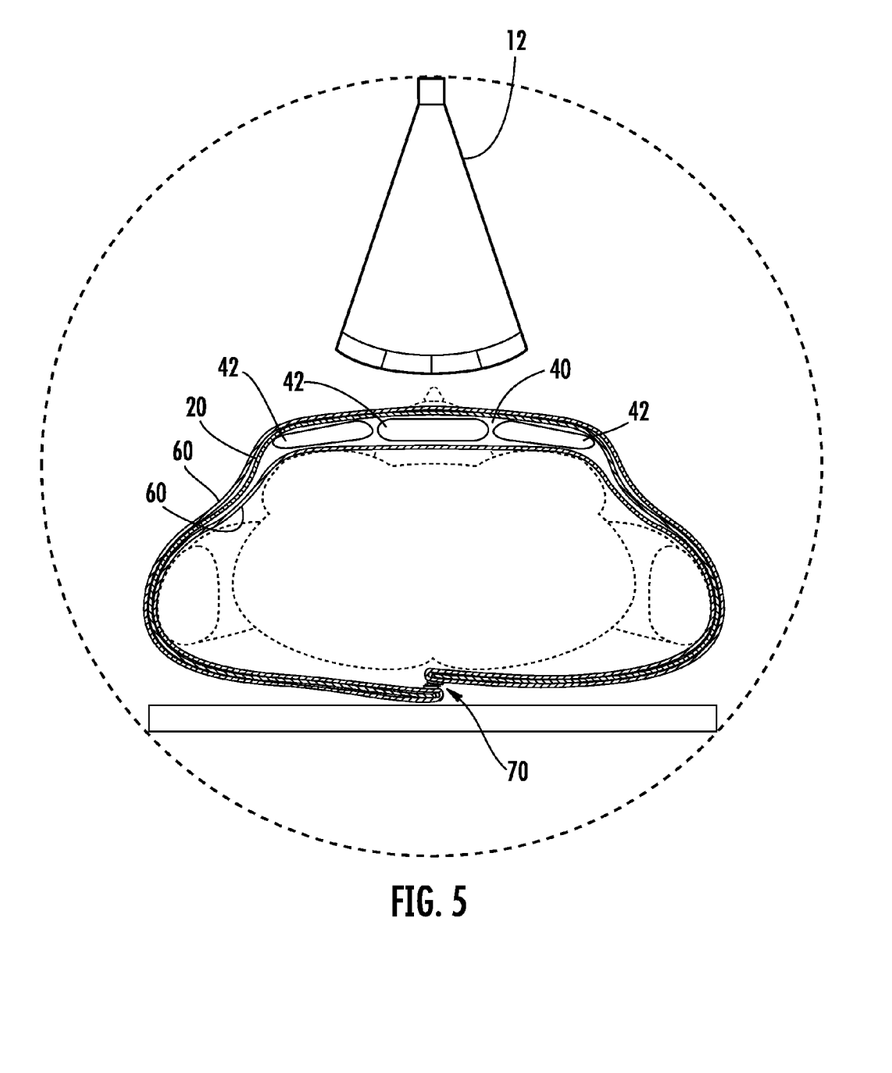
FIG. 5 is a cross sectional view of the radiation attenuation shield and a patient undergoing a CT procedure.

Referring to FIG. 5, barrier 20 is intended to be positioned (e.g., disposed, supported, placed, etc.) coincident with (e.g., in line with, in plane with, etc.) a primary radiation beam 12 to attenuate the primary radiation beam before reaching a target area (i.e., the area of examination) on a patient. Barrier 20 attenuates only a portion of the radiation and allows an amount of radiation sufficient to generate an image to penetrate the system (and subsequently the patient) to generate an image that can be viewed by a worker (e.g., surgeon, physician, technician, etc.). In this manner, shield 10 reduces the patient's radiation exposure by protecting the target area of the patient which is traditionally exposed (e.g., uncovered, unprotected, etc.) to the primary radiation beam.

In addition to protecting the patient, barrier 20 may also protect one or more individuals present during the radiological examination (e.g., physicians, surgeons, technicians, etc.). Individuals present during a radiological examination may also be susceptible to radiation exposure from the primary radiation beam (e.g., during a fluoroscopy procedure, etc.), but are more likely to be susceptible to radiation exposure from incidental scatter radiation. Barrier 20 protects against scatter radiation by absorbing at least a portion of the primary radiation beam and scatter radiation.

Barrier 20 may be configured to attenuate the flux of electromagnetic radiation over a broad wavelength range depending on the intended application. For example, barrier 20 may attenuate radiation from wavelengths of around $1.0 \times 10^{-15}$ meters (e.g., cosmic rays) to around $1.0 \times 10^{6}$ meters (e.g., radiation from AC power lines) including visible and invisible light, and may find incidental uses at relatively low or high frequency extremes (including gamma rays). The degree of radiation transmission attenuation factor by barrier 20 will depend in part on the specific application to which shield 10 is utilized. According to an exemplary embodiment, barrier 20 has a radiation attenuation factor that remains substantially constant throughout the entire layer. According to another exemplary embodiment, the radiation attenuation factor of barrier 20 varies depending on its position within shield 10. For example, a portion of barrier 20 that is intended to cover a target region on a patient may have a first radiation attenuation factor while a portion of barrier 20 that wraps around and covers non-target regions on a patient, but is still in-line with the primary beam 12 as it revolves around the patient (shown as a region 80 in FIGS. 2 through 4), may have a second radiation attenuation factor. Stated another way, the portion of barrier 20 that is offset from the patient by buffer 40 may have a first radiation attenuation factor while a portion of barrier 20 that is closer to the patient may have a second radiation attenuation factor. According to an exemplary embodiment, the second radiation attenuation factor may be less than the first radiation attenuation factor, at least in some areas such as an area opposite the target area, to allow a sufficient amount of the radiation to reach a sensor of the CT scanner used in generating an image of the patient.

According to one embodiment, barrier 20 has a radiation attenuation factor of a percent (%) greater than about 10% of a primary 100 kVp x-ray beam. According to other suitable embodiments, barrier 20 has a radiation attenuation factor of a percent of about 10-50%. According to further suitable embodiments, barrier 20 has a radiation attenuation factor greater than about 50%, suitably greater than about 90%, suitably greater than about 95%, at least in the area configured to cover the target area. According to a preferred embodiment, barrier 20 has a radiation attenuation factor of around 20-60%. According to still further suitable embodiments, barrier 20 may have radiation attenuation factors less than 10% or greater than 95% depending on the application. Barrier 20 may also at least partially attenuate gamma rays, and may have a gamma ray attenuation fraction of at least about 10% of a 140 keV gamma radiation source.

Barrier 20 may be fabricated from of any radiation attenuation material including, but not limited to, bismuth, barium, lead, tungsten, antimony, copper tin, aluminum, iron, iodine, cadmium, mercury, silver, nickel, zinc, thallium, tantalum, tellurium, and/or uranium. Anyone of the aforementioned attenuation materials alone or in a combination of two or more of the attenuation materials may provide the desired attenuation.

Barrier 20 may have a composition that includes only a radiation attenuation material or combinations thereof, or alternatively, barrier 20 may have a composition that includes a combination of a radiation attenuation material and a non-radiation attenuating material. For example, barrier 20 may include one or more radiation attenuation materials compounded (e.g. mixed, blended, alloyed, dispersed, layered, etc.) with a relatively non-radiation attenuating carrier material. According to one embodiment, barrier 20 has a composition similar to the radiation attenuation system disclosed in U.S. Pat. No. 4,938,233, which is hereby incorporated by reference in its entirety. According to another embodiment, barrier 20 has a composition similar to the radiation attenuation system disclosed in U.S. Pat. No. 6,674,087, which is hereby incorporated by reference in its entirety. However, it should be noted that barrier 20 is not limited to such embodiments. Barrier 20 be provided as a relatively single body, or alternatively may include a plurality of members (e.g., multiple layers of attenuating films or sheets stacked (e.g., overlapping) relative to each other). Forming barrier 20 as a plurality of members may provide a simple technique for varying the radiation attenuation factor along the barrier if such variation is desired. Of course, any other technique may also be used to vary the radiation attenuation factor (e.g., forming the material with different radiation attenuation factors, changing the thickness of the material, forming apertures in the material, etc.).

According to one embodiment, barrier 20 is a relatively light weight and flexible. Configuring barrier 20 as a flexible member allows provides for optimized workability for processing, bending, folding, rolling, shipping, etc. Barrier 20 may be formable (e.g. deformable) or compliant, and relatively stretchable (e.g. elastic). In this manner, barrier 20 can advantageously conform to the contours of the patient and wrap around the patient when placed thereon.

Still referring to FIG. 5, barrier 20 includes a first surface 22 (e.g., outer surface, upper surface, etc.) and a second surface 24 (e.g., inner surface, lower surface, etc.). Primary radiation beam 12 enters shield 10 through first surface 22 of barrier 20 and does not penetrate a target area on the patient until passing through second surface 24 of barrier 20. The amount of radiation penetrating the target area (radiation exiting second surface 24 of barrier 20) is less than if barrier 20 was not provided.

The interaction between the primary radiation beam and barrier 20 generates glare (noise, scatter, artifact, etc.), referred to generally as interference. Such interference traditionally limited the use of radiation barriers or shields over or near the target area. To prevent the interference from degrading the clarity and/or accuracy of an image generated by a radiological examination, shield 10 includes buffer 40.

As illustrated in FIG. 5, buffer 40 is provided between barrier 20 and the patient. In particular, buffer 40 is provided between barrier 20 and the patient at the target area on the patient. Buffer 40 lifts barrier 20 away from the patient and provides a relatively non-radiation attenuating boundary or zone between barrier 20 and the target area. Providing a non-radiation attenuating zone between barrier 20 and the target area is intended to improve the image quality of the surface regions of the patient or region slightly below the surface that would otherwise be non-viewable due to the interference generated when the radiation encounters barrier 20. Buffer 40 offsets barrier 20 outwardly from the patient a distance sufficient so that the interference does not prevent a readable image from being obtained. Buffer 40 may also advantageously reduce the radiation dose leaving the patient by providing increased absorption. While buffer 40 is only shown at the target area, according to the various alternative embodiments, buffer 40 may extend around the entire shield 10 similar to barrier 20.

Buffer 40 is formed of one or more relatively non-radiation attenuating materials. While buffer 40 may attenuate a certain amount of radiation, it is chosen for having relatively low radiation attenuating properties in comparison to barrier 20. According to an exemplary embodiment, buffer 40 comprises one or more receptacles (e.g., containers, pouches, compartments, etc.), show as bags 42, configured to hold a fluid. According to the embodiment illustrated, buffer 40 includes three bags 42, each bag 42 is configured to receive and selectively retain the fluid, such as air or any other gas, liquid or gel suitable for providing a relatively non-radiation attenuation buffer region between barrier 20 and the patient. During use, the three bags 42 are located above the target area on the patient. According to the various alternative embodiments, buffer 40 may be formed a variety of other non-radiation attenuation materials including, but not limited to, a polymeric material such as a foam material (e.g., closed cell foam, open cell foam, etc.), any woven or non-woven textile, cloth, fiber, vinyl, nylon, etc. Anyone of the aforementioned relatively non-radiation attenuation materials alone or in a combination of two or more of the non-radiation attenuation materials may provide the desired buffer 40.

Figure 7:
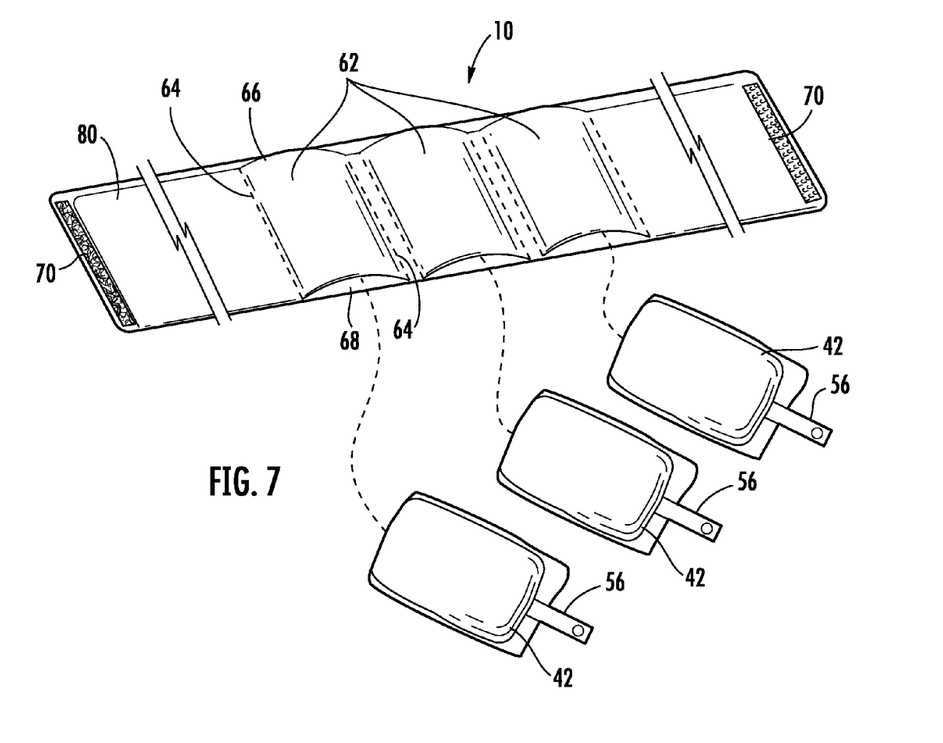
FIG. 7 is a partially exploded perspective view of the radiation attenuation shield illustrated in FIG. 1 illustrating the location of the fluid-filled bags.

Referring to FIG. 7, bag 42 is a flexible bag that includes first 44 and second 46 bag panels having peripheral edges 48 sealed together to define an inflatable chamber therebetween. A bag opening 50 extends through a portion of sealed edges 48 for receiving a fluid (e.g., air, etc.) to inflate the chamber. According to an exemplary embodiment, first 44 and second 46 bag panels are formed of a film material suitable for retaining the gas. First 44 and second 46 bag panels may be formed of any of a variety of suitable materials including, but not limited to, plastics such as a thermoplastic polymer, cellophane, etc.

The size, shape, and configuration of bag 42 will vary depending on the intended use of shield 10. According to the embodiment illustrated, bag 42 has a substantially rectangular shape, but accordingly to the various alternative embodiments, bag 42 may be formed of any shape with any number of panels so that bag 42 adequately provides the desired buffering region. According to an exemplary embodiment, bag 42 has a width extending parallel to a long side of shield 10. The width of bag 42 may varying depending on the overall length (i.e., side-to-side dimension) of shield 10. Bag 42 has a length extending parallel to a short side of shield 10 that is approximately equal to the overall width of shield 10 (i.e., top-to-bottom dimension).

According to one nonexclusive embodiment, bag 42 has a width that is between approximately 10 and approximately 20 centimeters when inflated, and a length that is between approximately 20 and approximately 40 centimeters when inflated. Dimensioning bag 42 within such ranges is intended to reduce the amount of radiation that is attenuated by buffer 40 by increasing ratio of gas to material used to form bag 42. According to the various alternative embodiments, bag 42 may have a width and/or a length that is less than or greater than the dimensions provided above. Further still, while buffer 40 is shown as utilizing three bags 42, buffer 40 may comprise any number of bags 42, including a single bag 42. However, providing a number of smaller individual bags 42, rather than a single bag as the buffer layer, may improve the ability of buffer 40 to conform to the contours of the patient.

Referring to FIG. 7, bags 42 are configured to be received within cover 60 of shield 10 and are shown as being spaced apart in lateral direction along shield 10. As detailed below, cover 60 includes individual openings or compartments that receive bags 42 and separate adjacent bags 42 from each other with a slight space or gap provided therebetween. Providing a space or gap between each bag 42 may further allow buffer 40 to better conform to the patient. According to an alternative embodiment, each bag 42 may interface with an adjacently positioned bag 42 and/or may be coupled to an adjacently positioned bag 42. According to a further alternative embodiment, a bag 42 may be fluidly coupled to one or more of the other bags 42. In such an embodiment, the fluid pressure would be substantially the same within all of the fluidly coupled bags 42.

Bag 42 is shown as having a first surface 52 and a second surface 54. According to an exemplary embodiment, second surface 54 of bag 42 is positioned adjacent to second surface 24 of barrier 20, while first surface 52 of bag 42 is intended to be positioned adjacent to the patient. Second surface 54 of bag 42 may contact second surface 24 of barrier 20, or alternatively, an intermediate layer or gap may be provided between second surface 24 of barrier 20 and second surface 54 of bag 42. Similarly, first surface 52 of bag 42 may be configured to contact the patient, or alternatively, an intermediate layer (e.g., a cover material, etc.) or gap may be provided between first surface 52 of bag 42 and the patient.

The distance that barrier 20 is offset from the patient depends at least in part on the state of inflation/deflation (e.g., thickness, etc.) of bag 42. This distance may vary depending on whether bag 42 is deflated, partially inflated or fully inflated. Preferably, barrier 20 is offset (e.g., spaced-apart) from the patient a distance sufficient to obtain an image of the patient without undue artifact or noise. That distance depends on a number of factors such as the radiation attenuation factor of barrier 20, physical characteristics of the patient (e.g., size, weight, etc.), and/or the region of the patient being examined (e.g., slightly below the surface, internal portions, etc.). According to an exemplary embodiment, bag 42 is sized to offset barrier 20 between approximately 0.1 centimeters (e.g., when substantially deflated) and approximately 30 centimeters from the patient (e.g., when fully inflated). According to a preferred embodiment, bag 42 is sized to offset barrier 20 up to approximately 10 centimeters from the patient (e.g., when fully inflated). The distance between barrier 20 and the patient may be defined by the thickness of bag 42 alone, or alternatively, shield 10 may include intermediate or supplemental layers or components (e.g., a cover material, etc.) that further add to the distance.

Bag 42 may be configured so that the pressure and/or volume of fluid within the bag is adjustable or nonadjustable. Providing a bag 42 wherein the pressure and/or volume is nonadjustable may reduce manufacturing costs by eliminating the need to provide a means for adjustment. However, in certain applications it may be beneficial to allow for the selective control of the pressure and/or volume within bag 42. For example, over time the bag 42 may leak and the pressure and/or volume of the fluid within the bag may lessen or otherwise change (thereby reducing the effective thickness of buffer 40) and sometime thereafter it may be desirable to return bag 42 to its initial state. Further, by selectively increasing or decreasing the pressure and/or volume of the fluid within the bag 42, the thickness of buffer 40 may be controllable thereby allowing the distance between barrier 20 and the patient to be selectively controlled by a user.

For various reasons (e.g., type of examination, size of patient, intensity of primary radiation beam, radiation attenuation factor of barrier 20, etc.) it may be beneficial to control the distance between barrier 20 and the patient. By allowing a user to selectively control the pressure and/or volume of the fluid within bags 42, and thereby control the positioning of barrier 20, a single shield 10 may be suitable for use with a variety of applications which call for varying the position of barrier 20. Referring back to FIG. 6, bag 42 is shown as having a device or mechanism (e.g., regulator, etc.), shown as a valve 56, suitable for allowing a user to selectively control the pressure and/or volume of the fluid (e.g., air, etc.) within each bag 42.

Figure 6:
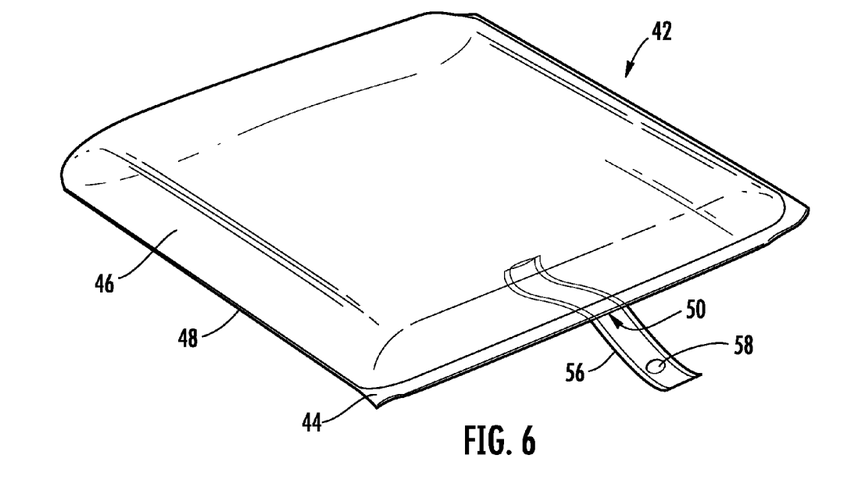
FIG. 6 is a perspective view of a fluid-filled bag according to an exemplary embodiment.

According to a preferred embodiment, valve 56 can be used by the medical personnel using shield 10 to selectively inflate or deflate bag 42. Valve 56 is selectively moveable between an open position and a closed position. Valve 56 is operably coupled to bag 42 at opening 50 and is shown as being disposed along an edge 48 that faces an edge of shield 10 that is intended to extend substantially perpendicular to the patient. Providing valve 56 along such an edge 48 allows the user (e.g., physician, medical assistant, technician, etc.) to more easily access valve 56 during a radiological examination. To inflate bag 42 (i.e., to increase the distance that barrier 20 is offset from the patient), the user can insert a fluid source (e.g., an air source, etc.) into an opening of valve 56 that is in fluid communication with the chamber of bag 42. For example, the user can insert a straw into the opening of valve 56 and blow air into the chamber. Alternatively, the user can insert a nozzle coupled to a medical facilities air source into the opening. To deflate bag 42 (i.e., to decrease the distance that barrier 20 is offset from the patient), the user can open valve 56 to reduce the pressure and/or volume of the fluid within the chamber. For example, the user can open valve 56 by manipulating the valve with their fingers (e.g., pinching, etc.).

Referring back to FIGS. 3 and 4, cover 60 is shown according to an exemplary embodiment. Cover 60 forms an exterior portion or surface of shield 10 and is useful in retaining and/or supporting bags 42, protecting barrier 20 bags 42 from contaminants (e.g., fluids, particles, etc.), providing enhanced comfort for a patient and improving the overall durability of shield 10. Cover 60 is shown as encapsulating both barrier 20 and bags 42 to define the entire exterior portion of shield 10. According to the various alternative embodiments, cover 60 may only cover either barrier 20 or bags 42, and as such, would only partially define the exterior of shield 10. According to the embodiment illustrated, cover 60 includes a plurality of pockets (e.g., envelopes, etc.), shown as compartments 62, for receiving bags 42. Each compartments 62 is defined by a pair of longitudinally extending boundaries, shown as seams 64, and a laterally extending boundary, shown as a seam 66, extending therebetween along at a bottom edge of the compartment. An upper edge of compartment 62 is left open so that bag 42 can be easily added to and removed from compartment 62 as shown in FIG. 7. Seams 64 and 66 may be formed by stitching or any other suitable coupling technique.

According to an exemplary embodiment, compartment 63 is sized to receive a single bag 42. If bag 42 includes valve 56, bag 42 should be inserted into compartment 62 in such a manner so that valve 56 is readily accessible through the opening of compartment 62. Positioning bag 42 in this manner will allow a user to adjust the positioning of barrier 20 relative to the patient without requiring the user to remove bags 42 from compartments 62. To conceal or hide valve 56, and/or to simply conceal and retain bag 42, cover 60 includes a supplemental covering or flap 68 movable between a first position wherein valve 56 is accessible to a user and a second position wherein pressure regulator is concealed from the user. Flap 68 may help protect against an inadvertent actuation of valve 56 during a radiological examination.

Cover 60 may be provided as a single unitary body integrally formed with barrier 20 and buffer 40, or alternatively, cover 60 may be provided as one or more sections positioned around buffer 20 and/or barrier 40 and coupled together. According to an exemplary embodiment, cover 40 is coupled to (e.g., bonded, fused, adhered, fastened, attached, connected, enclosing, etc.) barrier 20 employing any of a variety of suitable techniques. Cover 60 may be permanently coupled to barrier 20 and/or buffer 40, or alternatively, may be configured to be detachably coupled. Providing cover 60 as a detachable member may allow barrier 20 and/or buffer 40 to be conveniently interchangeable and/or replaceable. According to other suitable alternative embodiments, cover 60 may be disposed about barrier 20 without actually being coupled (either directly or indirectly) to barrier 20.

According to an exemplary embodiment, cover 60 may also include a fastening device to allow shield 10 to be secured to a patient. According to the embodiment illustrated, cover includes a hook and loop fastener 70 with corresponding sections provided at opposite lateral free ends of cover 60. Once shield 10 is wrapped around the patient, the corresponding sections of hook and loop fastener 70 can be joined to provide an appropriate fit as shown in FIGS. 2 and 5. According to the various alternative embodiments, hook and loop fastener 70 may be replaced with any of a number of attachment devices including, but not limited to, adhesives, clips, snaps, buttons, zippers, etc.).

Cover 60 may be made from a variety of materials. For example, cover 60 may be made of a material that enhances processability, softness or comfort for a user, a material that is substantially impervious to fluid, and/or a material having heat sealing properties to assist in the retention of body heat. Cover 60 may be fabricated from a variety of woven or non-woven materials including, but not limited to, polymers, natural fibers (cotton, wool, silk, etc.), nylon, vinyl, or composite materials. Cover 60 may further include an absorbent layer for maintaining fluid control (e.g., block blood from seeping onto the patient during a surgical procedure, etc.). The absorbent layer may be attached to a relatively liquid impervious layer such as a plastic, polyethylene, etc. The impervious layer may hinder the transmission of fluid from the absorbent layer to cover 60.

Figure 8:
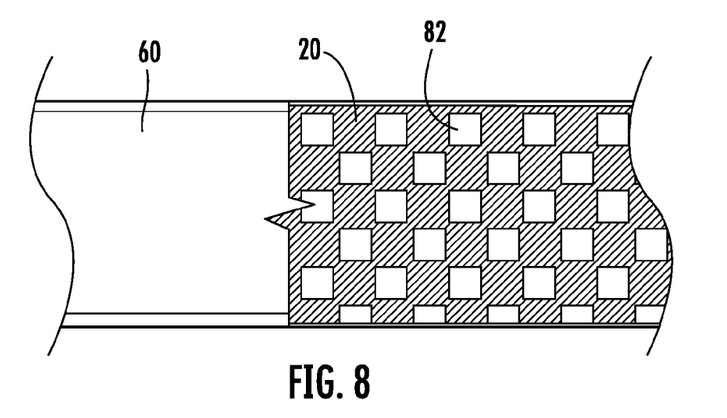
FIG. 8 is a fragmentary plan view of a radiation attenuation material provided at a rear portion of the radiation attenuation shield according to one exemplary embodiment.
Figure 9:
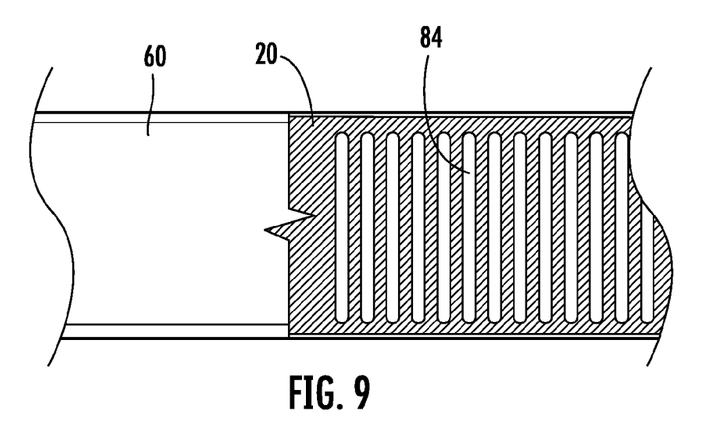
FIG. 9 is a fragmentary plan view of a radiation attenuation material provided at a rear portion of the radiation attenuation shield according to another exemplary embodiment.
Figure 10:
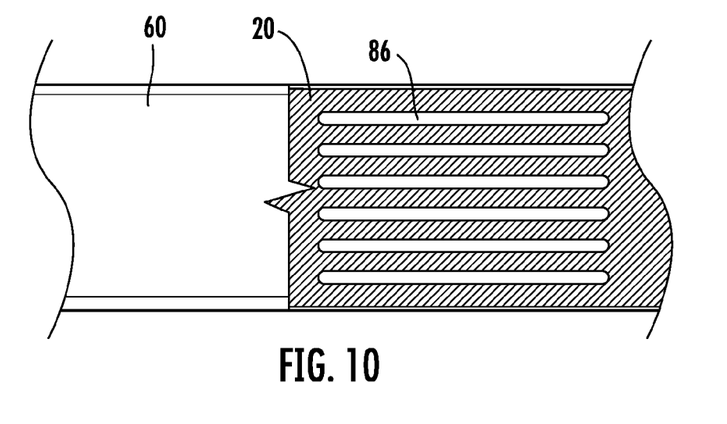
FIG. 10 is a fragmentary plan view of a radiation attenuation material provided at a rear portion of the radiation attenuation shield according to another exemplary embodiment.

Referring to FIGS. 8 through 10, further exemplary embodiments of shield 10 are shown. According to the exemplary embodiment of shield 10 shown in FIGS. 1 through 7, barrier 20 is a substantially solid layer as it extends between the lateral free ends of shield 10 even though, as noted above, barrier 20 may be formed of multiple layers and/or may have different thicknesses or compositions to provide for differing radiation attenuation factors. As also noted above, it may be desirable to provide barrier 20 with a radiation attenuation factor that is lower in those regions that are not offset from the patient by buffer 40. Such as region is identified in FIGS. 2, 3 and 7 as a region 80. Reducing the radiation attenuation factor of barrier 40 in these regions may further improve image quality, while still protecting the patient from undue exposure to radiation. The exemplary embodiments shown in FIGS. 8 through 10 provide an alternative approach to reducing the radiation attenuation factor of barrier 20 in region 80. In each embodiment, barrier 20 includes one or more apertures that allow the primary beam to pass through without being attenuated. Such a technique has been found to reduce the effective radiation attenuation factor of barrier 20. In such embodiments, barrier 20 remains a substantially solid layer in the region where barrier 20 is offset by buffer 40 (i.e., those regions intended to cover the target area).

According to the embodiment illustrated in FIG. 8, barrier 20 includes a plurality of openings 82 that are arranged to form a checkerboard appearance. According to the embodiment illustrated in FIG. 9, barrier 20 includes a plurality of openings 84 extending substantially parallel to each other in a longitudinal direction of shield 10. According to the embodiment illustrated in FIG. 10, barrier 20 includes a plurality of openings 86 extending substantially parallel to each other in a lateral direction of shield 10. Barrier 20 may be formed with openings 82, 84 and 86, or alternatively, openings 82, 84 and 86 may be removed from barrier 20 after formation (e.g., by cutting, etc.).

It is important to note that the construction and arrangement of the elements of the radiation attenuation system as shown in the illustrated embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, or the length or width of the structures and/or members or connectors or other elements of the system may be varied.

Also, for purposes of this disclosure, the term "coupled" means the joining or combining of two members (e.g., portions, layers, materials, etc.) directly or indirectly to one another. Such joining or combining may be stationary in nature or movable in nature. Such joining may be achieved with the two members or the two members and any additional intermediate members being integrally formed as a single unitary body with one another or with the two members or the two members and any additional intermediate member being attached to one another. Such joining or combining may be permanent in nature or alternatively may be removable or releasable in nature.

Further, the size, shape, and configuration of shield 10 may be provided in any number of forms (only a few of which are illustrated in the FIGURES) suitable for at least partially covering an article such as the anatomy of a patient or portions thereof. While shield 10 shown as being a substantially rectilinear cover, shield, or drape having a sufficient width and length to span entirely across the patient and an operating table, shield 10 may be provided as any of a number of shapes and sizes.

Further still, shield 10 is configured to be relatively compliant in nature so that it can reside closely next to the body of the patient. Shield 10 is intended to be comfortable and fit positively against the undulating surface of the patient thus improving its stability while the surgical team is operating on the body of the patient. Preferably the coefficient of friction between shield 10 and the surface of the patient adds to that stability, preventing movement of the radiation attenuation system during the surgical procedure and further obviating the need to take extraordinary measures to prevent slippage or movement of the drape.

Further still, shield 10 may be configured to be disposable in whole or in part, thereby minimizing ancillary sources of contamination that may arise from multiple uses. For example, shield 10 may be configured to allow barrier 20 and cover 60 to be retained while bags 42 forming buffer 40 can be replaced and/or interchanged as desired. Further, shield 10 may be configured to allow barrier 20 and/or buffer 40 to be retained while cover 60 is replaced.

Components of shield 10 are preferably non-toxic, recyclable, and/or biodegradable. According to an alternative embodiment, the articles of radiation attenuation system may be reusable (e.g. for attenuation of radiation from atomic/nuclear disaster, clean up, rescue operations, etc.). According to a preferred embodiment, the articles of shield 10 (e.g., barrier 20, buffer 40, and/or cover 60, etc.) may be sterilized between uses to minimize the likelihood of bacteriological or virus contamination. Sterilization may be performed in any convenient manner, including gas sterilization and irradiation sterilization.

It should further be noted that the elements and/or assemblies of the system may be constructed from any of a wide variety of materials that provide sufficient strength or durability, in any of a wide variety of colors, textures and combinations. Accordingly, all such modifications are intended to be included within the scope of the appended claims. Other substitutions, modifications, changes and omissions may be made in the design, operating conditions and arrangement of the preferred and other exemplary embodiments without departing from the spirit of the appended claims.

The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating configuration and arrangement of the preferred and other exemplary embodiments without departing from the spirit of the inventions as expressed in the appended claims.

What is claimed is:

1. A system for attenuating a primary radiation beam applied to a target area on a patient for generating an image of the target area during radiological examination, the system comprising:
   a barrier formed of a radiation attenuation material and positionable over the target area to partially attenuate the primary radiation beam before the primary radiation beam reaches the target area, the barrier being configured to substantially extend around an entire periphery of the patient; and
   a buffer positionable between the barrier and the patient for offsetting the barrier from the patient, the buffer being discrete from the barrier and comprising at least one flexible bag configured to retain a fluid, wherein the at least one flexible bag is configured to improve a clarity of the image generated during the radiological examination.

2. The system of claim 1, wherein the at least one flexible bag is configured to be selectively inflated and deflated to adjust a height of the barrier relative to the patient.

3. The system of claim 2, further comprising a valve coupled to the at least one flexible bag that allows a user to selectively inflate and deflate the at least one flexible bag.

4. The system of claim 1, wherein the at least one flexible bag comprises a plurality of flexible bags positioned adjacent to each other.

5. The system of claim 1, further comprising a cover that substantially encloses the barrier and the buffer.

6. The system of claim 5, wherein the cover comprises a pocket configured to receive the at least one flexible bag.

7. The system of claim 6, wherein the pocket comprises a flap configured to selectively conceal an opening into the pocket, wherein the flap is configured to be selectively opened by a user to remove the at least one flexible bag from the pocket.

8. The system of claim 1, wherein the barrier comprises a first radiation attenuation factor at a region intended to be positioned over the target area and a second radiation attenuation factor at a region intended to be positioned away from the target area, the first radiation attenuation factor being greater than the second radiation attenuation factor.

9. The system of claim 8, wherein the second radiation attenuation factor is achieved by providing apertures in the barrier in the region intended to be positioned away from the target area.

10. The system of claim 9, wherein the apertures in the barrier form a checkerboard appearance in the region intended to be positioned away from the target area.

11. The system of claim 9, wherein the region intended to be positioned away from the target area is configured to cover a backside of a female patient undergoing a breast examination.

12. The system of claim 1, wherein the at least one flexible bag is configured to be filled with air.

13. The system of claim 1, wherein the buffer is only provided under the barrier in a region intended to be positioned over the target area.

14. A system for attenuating a primary radiation beam applied to a target area on a patient for generating an image of the target area during radiological examination, the system comprising:
   a barrier formed of a radiation attenuation material and positionable over the target area to partially attenuate the primary radiation beam before the primary radiation beam reaches the target area;
   a buffer separate from the barrier and positionable between the barrier and the patient for offsetting the barrier from the patient, the buffer comprising at least one flexible bag configured to retain a fluid; and
   a valve coupled to the at least one flexible bag to allow a user to selectively inflate and deflate the at least one flexible bag for adjusting a distance between the barrier and the target area, wherein the at least one flexible bag is configured to improve a clarity of the image generated during the radiological examination.

15. The system of claim 14, wherein the system is configured as a breast shield for use on a female patient.

16. The system of claim 14, wherein the barrier is configured to substantially extend around an entire periphery of the patient.

17. The system of claim 16, further comprising a fastener coupled to the system at a region intended to be positioned away from the target area for securing the system to the patient.

18. A method of performing a radiological examination of a target area on a patient with a primary radiation beam to generate an image of the target area, the method comprising:
   placing a radiation attenuation system on the patient, the radiation attenuation system comprising a barrier formed of a radiation attenuation material and a buffer formed separately from the barrier, the buffer comprising at least one flexible bag configured to retain a fluid;
   aligning the barrier to be in-line with the primary radiation beam so that the primary radiation beam passes through the barrier before reaching the target area; and
   positioning the at least one flexible bag between the barrier and the target area.

19. The method of claim 18, further comprising controlling at least one of a pressure and a volume of the fluid within the at least one flexible bag to adjust a distance between the barrier and the target area.

20. The method of claim 18, further comprising wrapping the barrier around an entire periphery of the patient.

21. A system for attenuating a primary radiation beam applied to a target area on a patient for generating an image of the target area during radiological examination, the system comprising:
   a barrier formed of a radiation attenuation material and positionable over the target area to partially attenuate the primary radiation beam before the primary radiation beam reaches the target area, the barrier being configured to extend around an entire periphery of the patient; and
   a buffer positionable between the barrier and the patient for offsetting the barrier from the patient, the buffer comprising at least one flexible bag configured to retain a fluid, wherein the at least one flexible bag is configured to improve a clarity of the image generated during the radiological examination.

* * * * *